(12) United States Patent
Haykeen

(10) Patent No.: US 8,869,415 B1
(45) Date of Patent: Oct. 28, 2014

(54) FOLDABLE PORTABLE WALL-MOUNTED HEIGHT MEASURING DEVICE TO MEASURE THE HEIGHT OF A PERSON, AND A STAMPED RECORDATION OF THE DATE THE HEIGHT MEASUREMENT WAS TAKEN

(71) Applicant: Zohar Haykeen, Valley Village, CA (US)

(72) Inventor: Zohar Haykeen, Valley Village, CA (US)

( * ) Notice: Subject to any disclaimer, the term of this patent is extended or adjusted under 35 U.S.C. 154(b) by 226 days.

(21) Appl. No.: 13/647,804

(22) Filed: Oct. 9, 2012

(51) Int. Cl.
*A61B 5/107* (2006.01)

(52) U.S. Cl.
CPC .................................. *A61B 5/1072* (2013.01)
USPC .................................. 33/512; 33/478; 33/485

(58) Field of Classification Search
CPC ........ A61B 5/1072; A61B 5/107; G01B 3/04; G01B 3/06
USPC .................................... 33/483, 485, 478, 512
See application file for complete search history.

(56) References Cited

U.S. PATENT DOCUMENTS

| | | | | |
|---|---|---|---|---|
| 2,215,884 A * | 9/1940 | Runge | ............................. | 33/512 |
| 4,008,524 A * | 2/1977 | Allen | ............................... | 33/512 |
| 4,713,888 A * | 12/1987 | Broselow | ........................ | 33/512 |
| 5,402,585 A * | 4/1995 | Lund | ................................ | 33/512 |
| 6,226,881 B1 * | 5/2001 | Landauer | ........................ | 33/515 |
| 6,599,045 B1 * | 7/2003 | Kolb | ............................... | 33/512 |
| 2004/0111909 A1 * | 6/2004 | Pourmanafzadeh | ........... | 33/512 |
| 2005/0210694 A1 * | 9/2005 | Leyden et al. | .................. | 33/492 |
| 2012/0144686 A1 * | 6/2012 | Haykeen | ........................ | 33/512 |
| 2012/0304476 A1 * | 12/2012 | Doppel et al. | .................. | 33/700 |
| 2014/0190029 A1 * | 7/2014 | Blakely | ........................... | 33/512 |

* cited by examiner

*Primary Examiner* — G. Bradley Bennett
(74) *Attorney, Agent, or Firm* — Thomas I. Rozsa

(57) ABSTRACT

A portable foldable height measuring device which can be removably mounted to a vertical surface such as a wall in order to measure the height growth of a person, primarily a child, to determine that the child is growing at a proper rate and to keep an accurate record of the child's height on a given date.

15 Claims, 10 Drawing Sheets

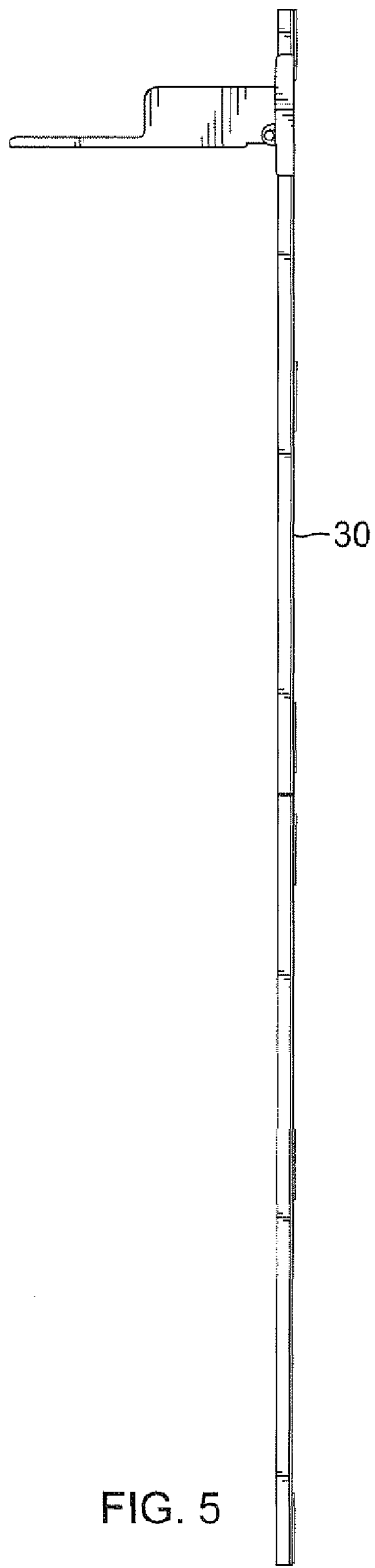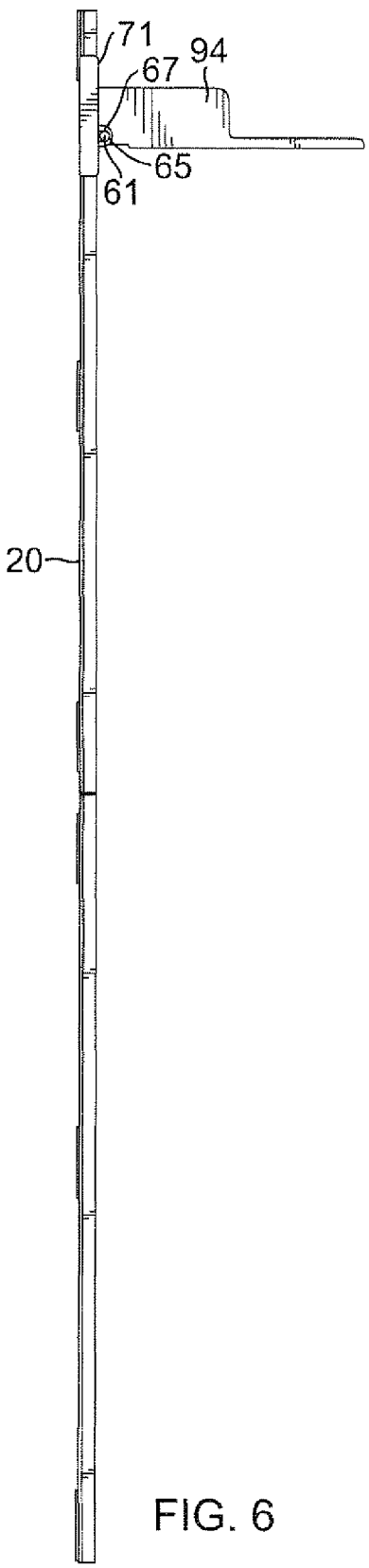
FIG. 5
FIG. 6

FOLDABLE PORTABLE WALL-MOUNTED HEIGHT MEASURING DEVICE TO MEASURE THE HEIGHT OF A PERSON, AND A STAMPED RECORDATION OF THE DATE THE HEIGHT MEASUREMENT WAS TAKEN

BACKGROUND OF THE INVENTION

1. Field of the Invention

The present invention relates to the field of measuring devices which are used to measure the growing height of a child so that a record can be kept on a periodic basis as to how quickly the child has grown and what height the child has achieved by a certain age and date.

2. Description of the Prior Art

Height is an important measurement for assessing the fitness of a person. A number of traditional height measuring devices have been developed in the art. These devices help the person to record progressive increases in height. Most conventional height measuring systems adopt a method in which a person stands against a wall and the person's height is marked on the wall. Such markings will fade over time and become lost.

The following four prior art patents are relevant to the present invention:

1. U.S. Pat. No. 4,008,524 issued to Allen on Feb. 22, 1977 for "GROWTH MEASURING SCALE" (hereafter the "Allen Patent").

2. U.S. Pat. No. 4,196,521 issued to Hutchinson et al. on Apr. 8, 1980 for "HEIGHT MEASURING DEVICE' (hereafter the "Hutchinson Patent").

3. U.S. Pat. No. 6,226,881 issued to Landauer on May 8, 2001 for "HEIGHT-MEASURING DEVICE" (hereafter the "Landauer Patent").

4. U.S. Pat. No. 7,059,060 issued to Baumgartner on Jun. 13, 2006 for "DEVICE FOR RECORDING EVENTS AND MEASURING GROWTH IN AN INDIVIDUAL'S LIFE" (hereafter the "Baumgartner Patent").

The Allen Patent discloses a wall mountable height measuring device which is designed to measure the height of several different children. The measuring device enables the user to measure a child's height and then a screw is screwed into the device to memorialize that the child's height was that specific height. There is no mechanism by which the date is recorded or stamped to be able to determine the date that the child was measured at a given height. Therefore, someone would have to separately record on a separate piece of paper or on a notebook what the date was when that height was taken and also separately record the name of the specific child. With respect to the technique in the Allen Patent, the name of the child is not listed but instead, a child is designated by a given color so that the screw that is screwed into the device is of the same color, for example, Nancy may be blue, Erie may be green, etc. It is a very inefficient and poor way of recording the height growth of a child because the date of the height measurement and the specific child's name for whom the height was recorded is not in an integral unit which is easy to locate and determine. Therefore, confusion can easily arise by somebody accidentally writing in a date of height based on color and accidentally using the wrong name because they misinterpreted the color that was assigned to that child.

The Hutchinson Patent describes a height measuring device that includes telescopically arranged measuring rods with faces containing parallel vertical columns of different types of height measuring units such as English measuring units and metric measuring units. However, this height measuring device is quite heavy and hence not portable.

The Landauer Patent describes a height-measuring device that is foldable, or collapsible, on itself, in order to provide an easier and less-costly method of packaging and shipping. The height measuring device consists of an extensible leg or setup section that is mounted in the rear of the scale-part. The extensible leg has a length equal to the lowest measurement reading of the scale-section. The bottom edge surface of the scale-part can be readily located during installation of the height measuring device. However, the device has no arrangement to record the date at which the height measurement was taken.

The Baumgartner Patent describes a device for recording both chronological events and physical growth events of an individual or group of individuals. The device includes a linear measuring device having at least first and second opposed sides. The first side has a linear measurement scale inscribed thereon and at least one recording surface associated therewith. The second side has a chronological scale, preferably in months and years, inscribed thereon and also has at least one recording surface associated with the chronological scale. Thus, physical growth can be measured on the first side and recorded on the recording surface associated therewith as the individual or several individuals grow. Significant events such as the date of height measurement can be recorded on the other side. However, this device has two separate sides for measuring height and date and both measurements cannot be recorded simultaneously. Further, the device is not wall mountable.

There is, however, a significant need for an improved height measuring device which is easily portable so that it can be transferred from one location to another and can be removably affixed to a vertical surface such as a wall and can also be transported so that it remains in a pristine condition to accurately record the height change of a person on a given date.

SUMMARY OF THE INVENTION

The present invention is a portable foldable height measuring device which can be removably mounted to a vertical surface such as a wall in order to measure the height growth of a person, primarily a child, to determine that the child is growing at a proper rate and to keep an accurate record of the child's height on a given date.

The height measuring device includes a pair of oppositely disposed vertical frame members with a parallel set of oppositely disposed height measurement scales, one in inches and one in centimeters. The height measuring scales are separated by a vertical marking surface so that a given date can be stamped at the location of a given height in order to record the growth of a child.

Press fit vertical sliding bars are movably attached to the respective vertical frames in a press fit manner so that the sliding bars can be slid up or down the distance of the vertical frames and remain stationary at a given point. The pair of sliding bars rotatably support a height measuring bar which has a planar surface and contains thereon a housing to permanently retain a stamping mechanism to record the dates. The housing contains a mechanism by which the stamp is permanently retained within the housing so that the same stamp can be used over and over again to record the changes in a child's height without the concern that the stamp will be lost or mislaid or modified to give an inaccurate reading.

It is an object of the present invention to provide a vertical height measuring device which has a center folding member so that the device can be folded in half to reduce its height from six feet to three feet so that it can be easily transported from one location to another or from one room to another if the family moves or has to relocate.

It is a further object of the present invention to provide a height measuring device which can be removably but firmly affixed to a vertical wall so that it can stay in place during the time that the child's height is being measured but can be moved from one location to another if necessity requires a movement because the family moves to a different location or for whatever reason it is determined that a different room is better for measuring the child's height.

It is a further object of the present invention to provide measuring scales of at least two different measuring denominations such as inches and centimeters so that the child's height can be recorded not only in the United States, but in foreign countries where centimeters are preferred over inches for measuring height.

It is an additional object of the present invention to provide a device that has a self-contained stamping mechanism within the leveling device so that a child's height can be accurately recorded with the same stamping device over and over again to provide consistency and to be sure that the stamping device is not altered or lost, requiring a different stamping device.

It is an additional object of the present invention to provide an enclosed marking system between the two scales so that the date stamp can be stamped at a specific height measurement when the child's height is taken and the height can be measured over certain periodic time periods that are set such as the first day of the month, the last day of the month, of sequentially between two or three months so that a consistent record of the child's growth is kept.

It is a further object of the present invention to have the date stamp permanently affixed to the actual measuring device by a housing mechanism which prevents the loss of the date stamp and prevents the modification of the date the height is measured so that there is a consistent and accurate record of the height development of the child as the child grow.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 5 is a right side elevational view of the present invention in its operating condition;

FIG. 6 is a left side elevational view of the present invention in its operating condition;

DETAILED DESCRIPTION OF THE PREFERRED EMBODIMENTS

Figure 1:
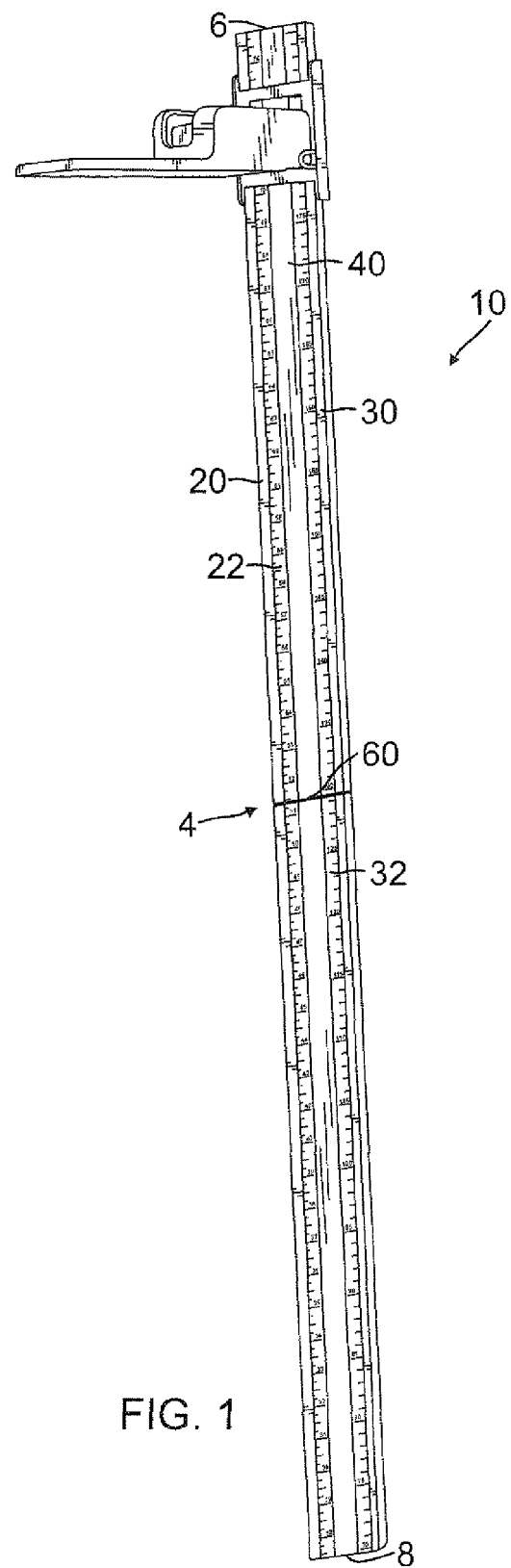
FIG. 1 is a perspective view of the present invention shown in the operating condition with the height measuring leveling platform and date stamp measuring system in an operating condition.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1-13, there is illustrated at 10 the present invention foldable portable wall-mounted height measuring device which is mounted to a wall to measure the height of a child on a given date on a periodic basis. The height measuring device 10 includes a first frame section 20 and an oppositely disposed second frame section 30, the pair of frame members 20 and 30 comprising vertically aligned frame sections. The vertically aligned frame sections 20 and 30 support a planar vertical section 40. To one side of the planar vertical section 40 is a first vertical measuring scale 22 inscribed into the planar vertical section 40 or affixed into the planar vertical section 40 adjacent first frame section 20, which first vertical measuring scale extends from the bottom 8 of the measuring device 10 to the top 6 of the measuring device 10. The first vertical measuring scale 22 can be in a certain denomination such as inches. Adjacent the second frame member 30 is a second vertical measuring scale 32 inscribed into the planar vertical section 40 or affixed into the planar vertical section 40 which contains height measuring denominations different from the first vertical measuring scale 22. By way of example, the second vertical measuring scale can be in centimeters and again, extends from the bottom 8 to the top 6 of the measuring device 10.

In between the two vertical measuring scales 22 and 32 on the vertical planar section 40 is a clear planar surface 50 onto which dates can be stamped to correspond to given heights on the vertical measuring scales 22 and 32.

Figure 11:
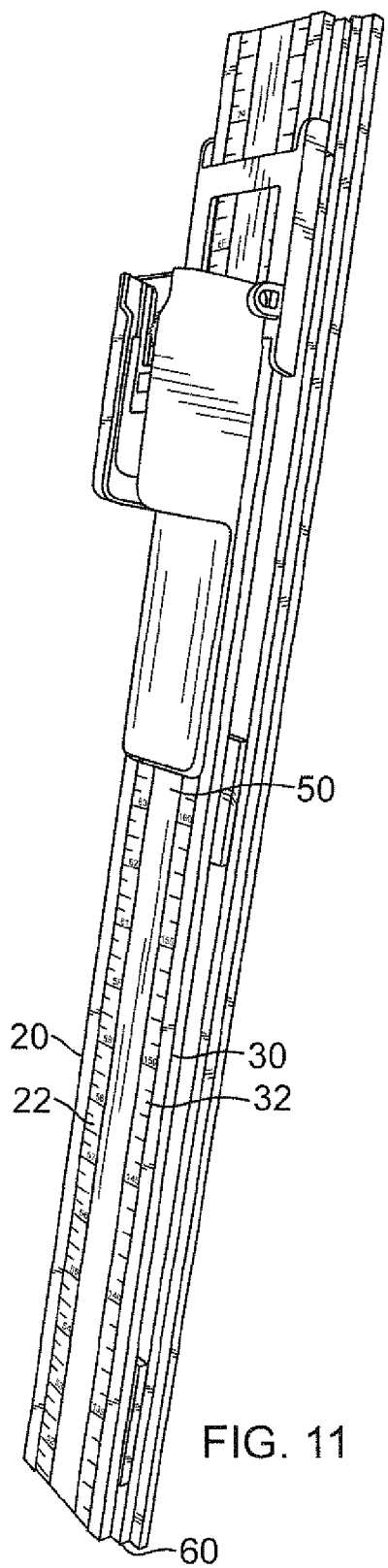
FIG. 11 is a perspective view of the present invention in the folded condition for easy transport, with the height level device in a folded condition.

The device 10 has a foldable mechanism 60 at the approximate midpoint 4 of the device 10 so that as illustrated in FIG. 11, the device can be folded in half for easy transport.

Figure 2:
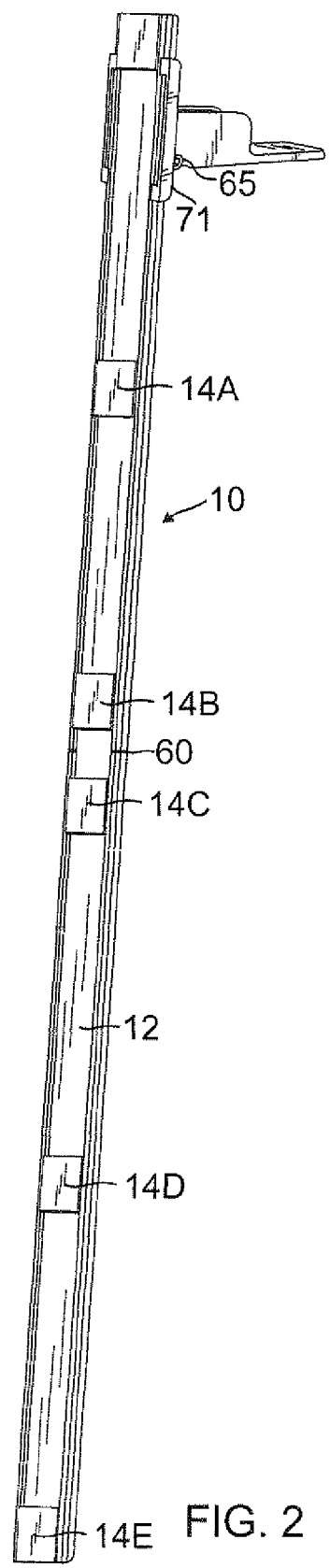
FIG. 2 is a rear perspective view showing the removable mounting mechanism of the present invention and the height measuring device and date stamp measuring system in the operating condition.
Figure 3:
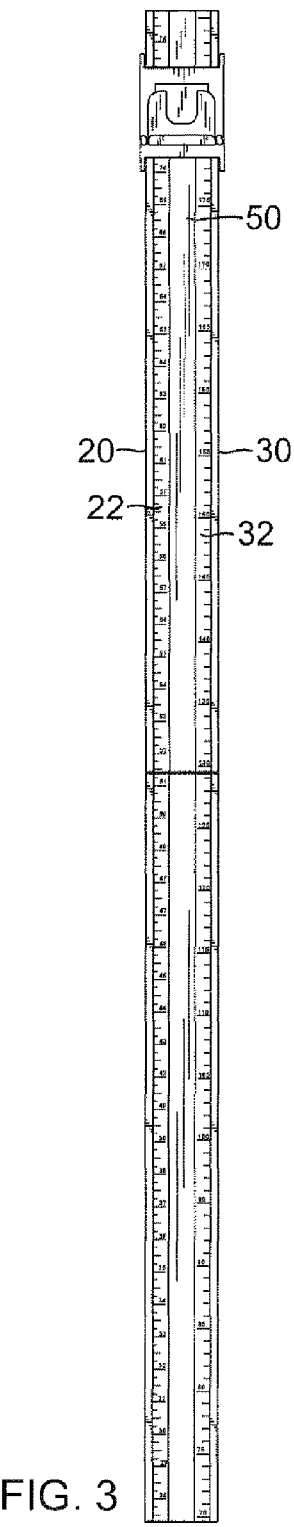
FIG. 3 is front elevational view of the present invention showing the height scales in two different measurement denominations in inches and centimeters and the height measuring device in its operating condition.
Figure 4:
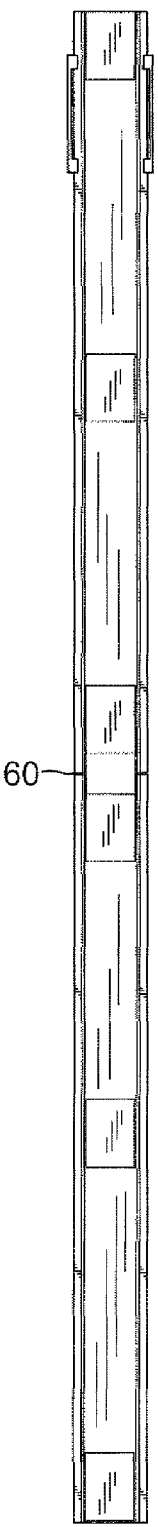
FIG. 4 is a rear elevational view of the present invention illustrating the removable mounting means and the rear portion of the attachment mechanism by which the height measuring device is affixed to the frame of the structure.
Figure 7:
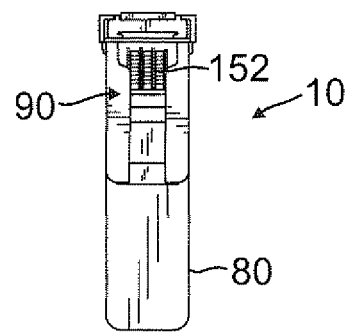
FIG. 7 is a top elevational view of the present invention.
Figure 8:
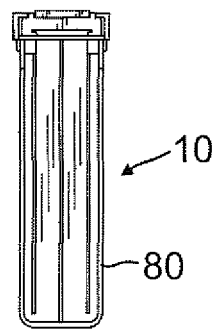
FIG. 8 is a bottom elevational view of the present invention.

Referring to the rear 12 of the assembly 10 as illustrated in FIG. 2, there are a multiplicity of movable mounting means 14A, 14B, 14C, 14D, 14E, which can be two-sided tape or other mechanisms by which the measuring frame 10 can be removably affixed to a vertical surface such as wall. The reason for being able to be removably affixed is that if the parents move, or it is determined that it is better to measure the child in a different room, then the entire assembly can be removed from the wall and re-affixed to a different wall at a different location.

Figure 12:
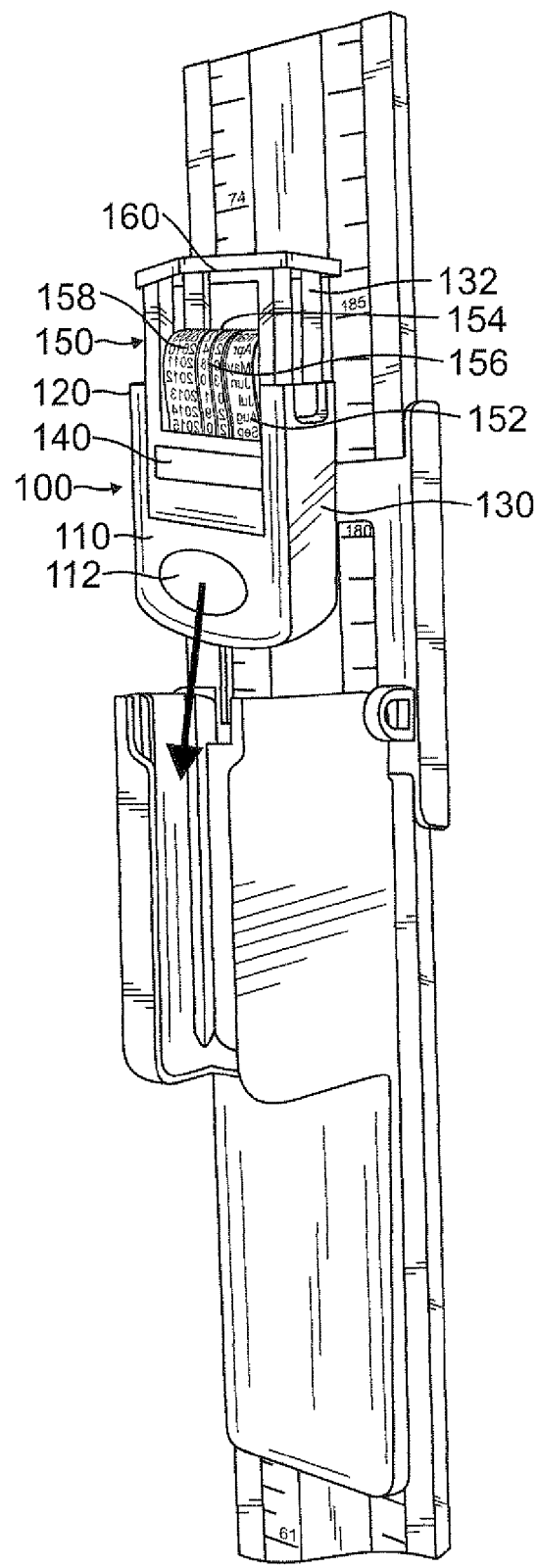
FIG. 12 is an enlarged, partially exploded, detail view of the height measuring device and the date stamp and the enclosure retaining the date stamp so it will not be lost.
Figure 13:
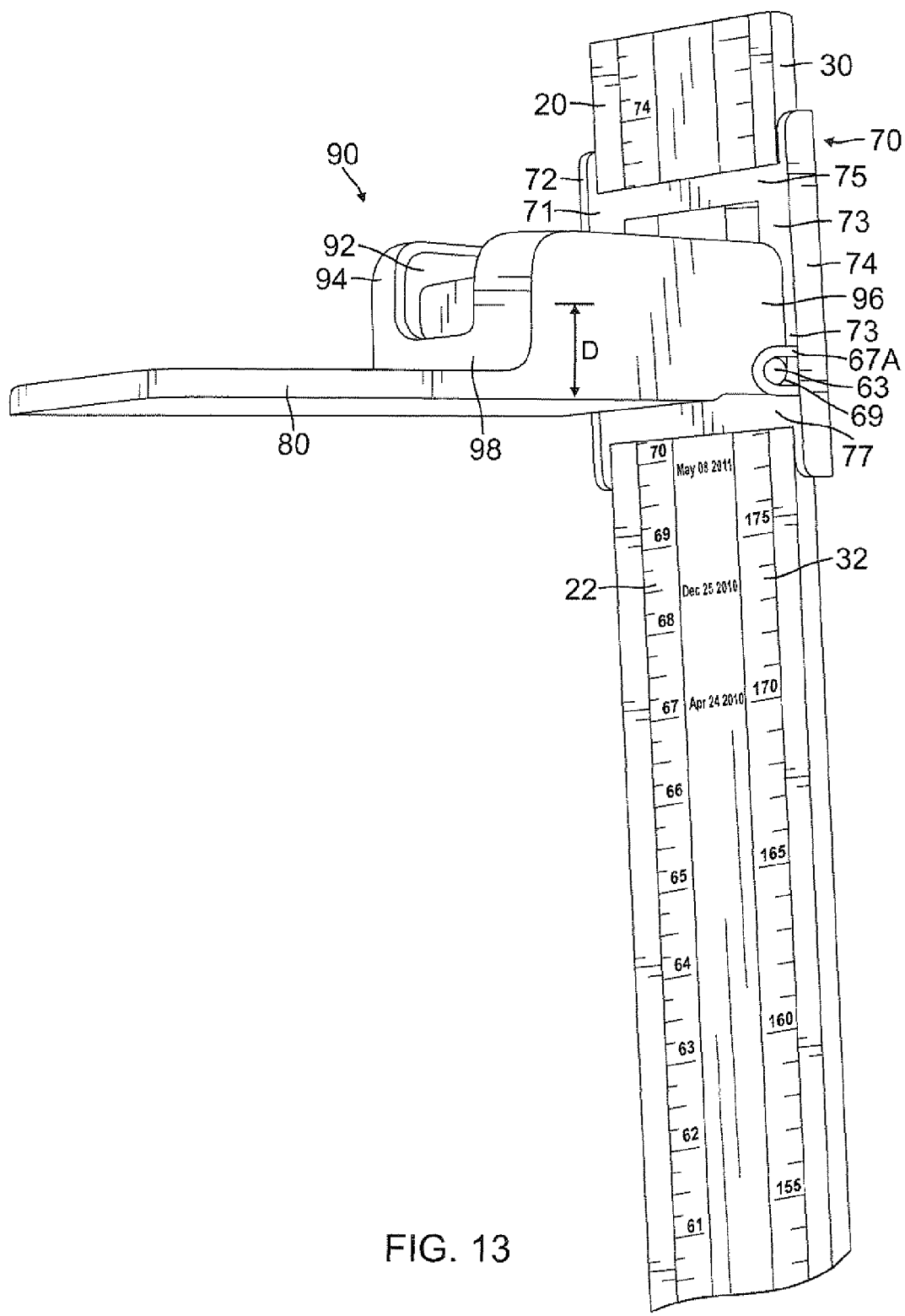
FIG. 13 is an enlarged, detail view of a portion of the present invention illustrating the measuring scales and a date stamped into the planar surface between the scales.

Referring to FIGS. 11 through 13, the device 10 also contains a movable height level retaining frame member 70 having a first outer sidewall section 72 which is wrapped around and slidably press fit onto first frame member 20 and a parallel oppositely disposed second outer sidewall section 74 which is wrapped around and slidably press fit onto second frame section 30 so that the movable height level retaining frame member 70 can be slid up and down the frame members 20 and 30 and remain affixed at a given section location. The movable height level retaining frame member 70 has a body comprising a first interior sidewall 71 parallel to and adjacent first outer sidewall section 72, a second interior sidewall 73 parallel to and adjacent second outer sidewall section 74, a first upper transverse wall 75 interconnecting interior sidewalls 71 and 73 and a parallel second lower transverse wall 77 interconnecting interior sidewalls 71 and 73. Referring to FIG. 6, first interior sidewall 71 retains a first transverse retainer 65 with an opening 67 to receive a transverse round pin 61 extending from housing sidewall 94 (see description below) and second interior sidewall 73 retains a second transverse retainer 67A with an opening 69 to receive a transverse round pin 63 extending from housing sidewall 96. The housing 90 is rotated about pins 61 and 63 so that it can be retained perpendicular to movable height level retaining frame member 70 as illustrated in FIG. 13 or retained parallel to height level retaining frame member 70 when not in as illustrated in FIG. 11 so that it is not in the way when not in use.

Figure 9:
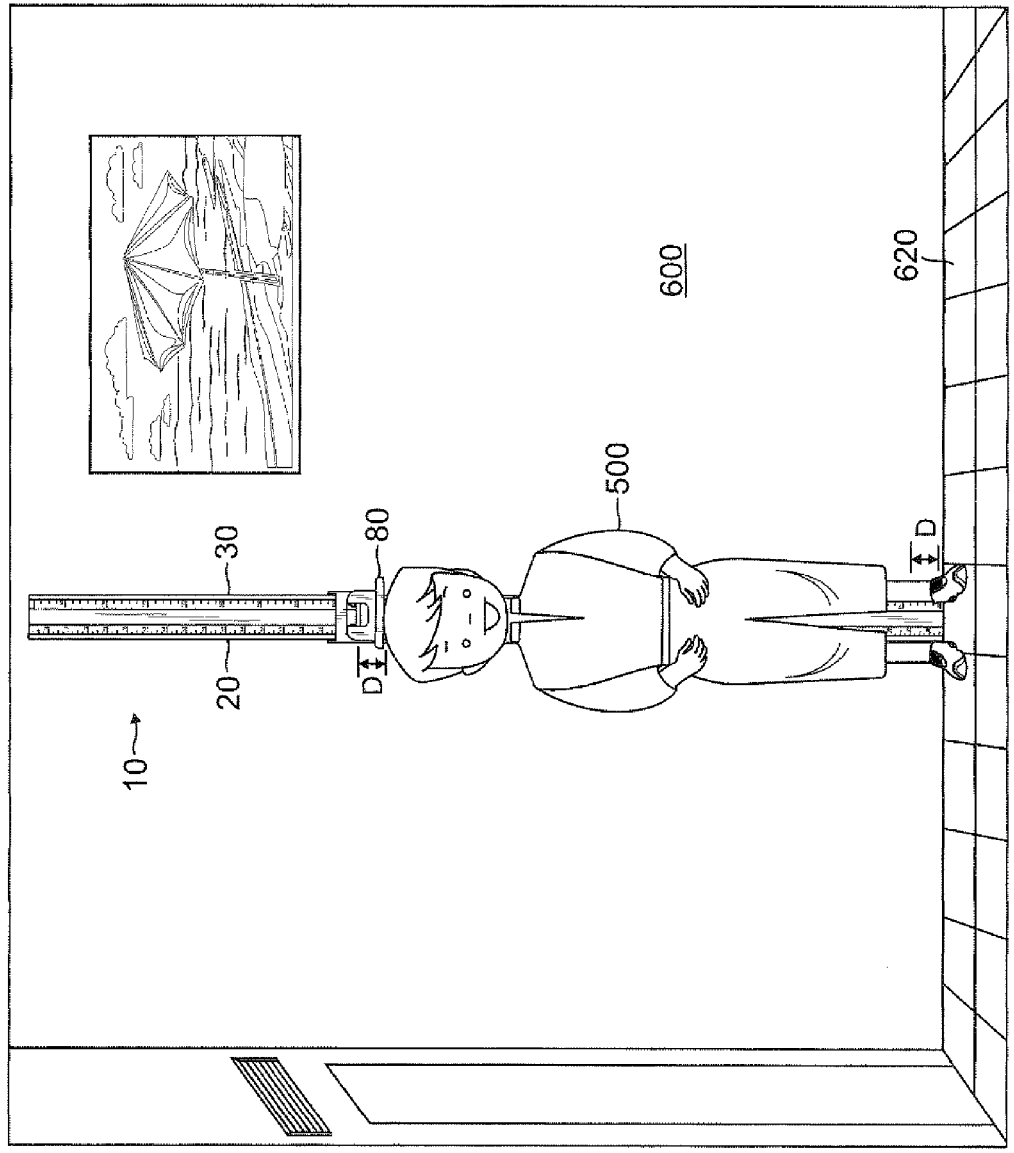
FIG. 9 is a view with a child standing against the present invention with the height leveling device positioned in line with the child's head and the date stamp in place.
Figure 10:
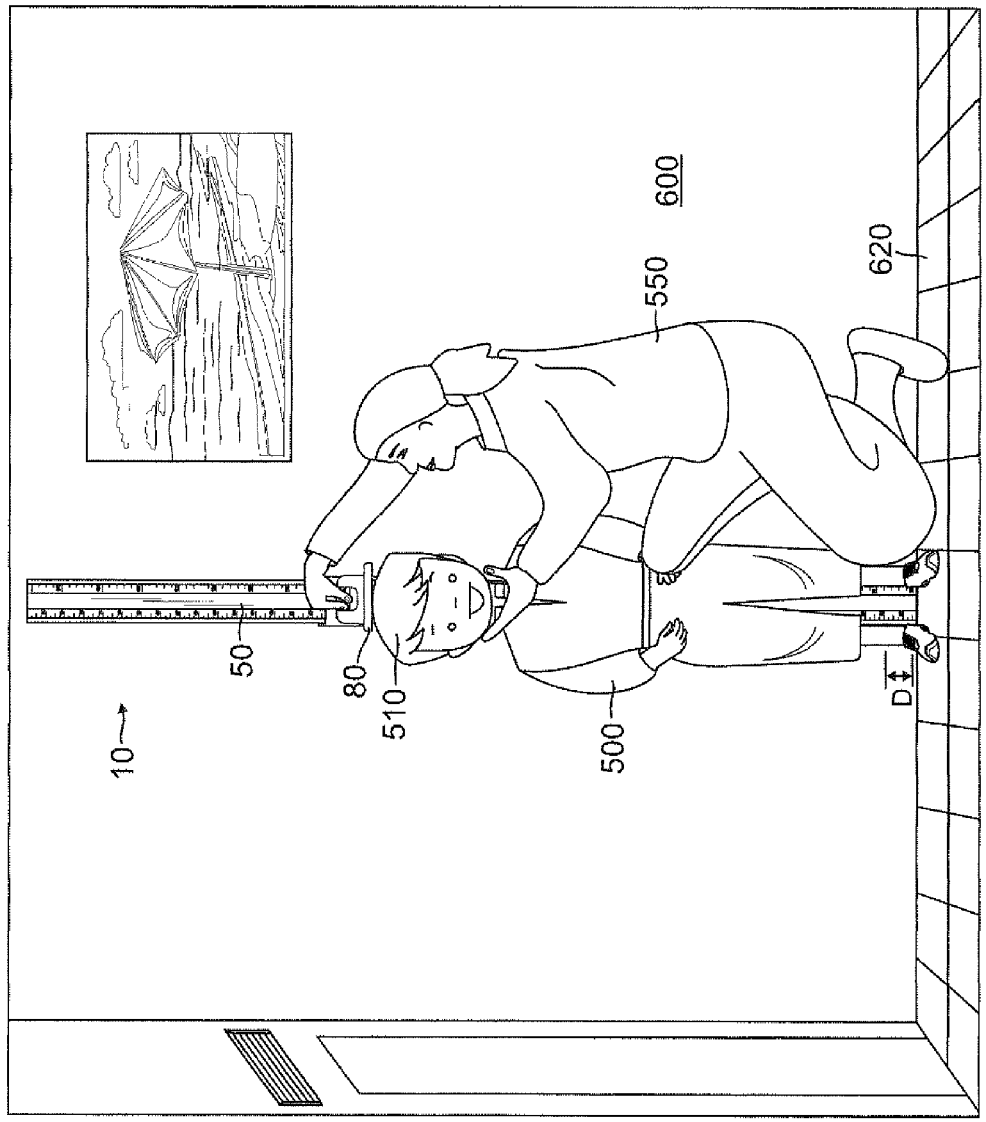
FIG. 10 is a view of a child's height being measured with a child standing against the present invention with the height leveling device positioned in line with the top of the child's head and the date stamp in its operating condition and with a parent recording a given date corresponding to the child's height on that date.

The movable height level retaining frame 70 contains a hingeably disposed height measuring bar 80 which is rotatable retained on the frame 70 so that the height measuring bar 80 can be rotated so that it is vertically oriented and parallel to the frame sections 20 and 30 when not in use as illustrated in FIG. 11 and can be rotated so that it is generally perpendicular to the frame sections 20 and 30 when in use as illustrated in FIGS. 9, 10 and 11.

Referring to FIG. 13, incorporated into and made a part of the height measuring bar 80 is a date stamp retaining housing 90 having a stamp mechanism retaining chamber 92 surrounded by sidewalls 94 and 96 and rear wall 98. Referring to FIG. 12, a date stamp retaining mechanism 100 comprises a body 110 with a thumb grip 112 and with sidewalls 120 and 130 surrounding an interior chamber 140 which retains a date stamp 150 having a date rotating mechanism 152 to change the month 154, day 156 and year 158. The sidewalls 120 and 130 contain respective slots (slot inside wall 120 not shown) and 132 which slide on interior retaining pins (not shown) within sidewalls 94 and 96. The date stamp 150 extends to an open wall section 160 between sidewalls 120 and 130. When the sidewalls 120 and 130 are pulled out of housing 100 by a thumb pressure pulling on thumb grip 112, the body 100 is moved along slots (first slot not shown) and 132 so that the date stamp 150 is aligned with open wall 160, when the height measuring bar 80 is rotated to a horizontal alignment perpendicular to the frame sections 20 and 30, the date stamp 150 can come in contact with clear planar surface 50. The housings 90 and 100 retains the date stamp 150 so that the date stamp 150 cannot fall out and so that the date stamp 150 can be inked when necessary to stamp a given date onto the clear planar surface 50.

The date stamp 150 is adjusted to the proper month 154, day 156 and year 158 and inked.

Referring to FIGS. 9 and 10, the height measuring device 10 is removably affixed to a wall 600. As is clearly visible from FIGS. 9 and 10, when the height measuring bar 80 is placed above the child's head, there is a distance between the horizontal height of the date stamp and the top of the child's head, which distance is "D". This is due to the fact that the date stamp must of necessity be in the housing and cannot be exactly on top of a child's head or otherwise the child's head would be filled with ink or their hair would be pulled out. Therefore, it is necessary that the date stamp be a given height distance "D" above the height of the child's head. In order to compensate for this, the device 10 is mounted above the floor of the room by the same given distance "D" to compensate for this difference between the actual height of the child's head and the height of the date stamp where the date is recorded onto the planar surface 50. By way of example only, the distance "D can be ⅝" so that the device 10 is mounted to the wall so that it is the distance "D", for example ⅝", above the floor 620.

Another way to achieve the same result is that the given height of the device at this time is 75⅜". Therefore, a person can take a ruler and measure the height of 76" so that the top of the device 10 is at 76" above the floor which in effect leaves a gap of ⅝" from the bottom of the device 8 and the floor 620. In this illustration, the distance "D" is ⅝" because that is the difference between the height of the date stamp and height of the child's head as measured by the leveling bar 80. It will be appreciated that this given distance can be any desired distance depending upon the configuration of the date stamp as it relates to the height of the child's head. Therefore, the distance "D" can vary anywhere from ⅛" to 1". At present, the preferred embodiment is ⅝" but it will be appreciated that any given distance is within the spirit and scope of the present invention.

A child 500 stands against frame sections 20 and 30. The height measuring bar 80 is rotated so that it s perpendicular to the frame sections 20 and 30 and perpendicular to the interior sidewalls 71 and 73 of the movable frame member 70. The first and second sections 72 and 74 are respectively slid on the frame sections 20 and 30 so that the height measuring bar 80 extends above the height of the child 500 and then the movable frame member 70 is slid down the frame sections 20 and 30 so that the height measuring device 80 rests immediately above the child's head 510.

As shown in FIG. 10, the parent 550 can then adjust the height measuring bar 80 so that it is exactly in the same place as the child and aligned with the top of the child's head. The date stamp housing 100 is pulled forward from the date stamp retaining housing 90. The date stamp 150 is at a downward angle so that the date stamp 150 can affix the date onto the planar surface 50 so that the child's given height on a certain day is recorded. The device 10 can be used over and over again as the child grows with the date stamp 150 stamped into the planar surface 50 to show the child's height on a given date.

As best illustrated in FIG. 13 already discussed, when the height measuring bar is rotated, the bracket 70 is exactly perpendicular to the surface 50 where the date stamp is recorded so that there is no inconsistency or mis-measurement because the date stamp is exactly perpendicular to the surface and therefore, a very accurate recording of the height is made. This perpendicular feature of the assembly 90 assures that the date stamp will not inadvertently be stamped at an angle up or at an angle down which would lead to an inaccurate recording but is instead exactly perpendicular to the surface 50 so that the exact height is accurately recorded.

Referring to FIGS. 9, 10 and 13, the accuracy of the measurement is further assured because when the height measuring bar 80 is against the head 510 of the child 500, the date stamp housing 90 bumps into the planar vertical sections 71 and 73 of bracket 70 and that causes the height measuring bar 80 to stop at 90 degrees (parallel to the floor 620) and that makes the measurement accurate. This feature causes the date stamp 150 and its month, day and year designations 154, 156 and 158 to be exactly perpendicular to the planar surface 50 where the date is marked. As a result, the measurement is completely accurate because the date is stamped exactly in line with the appropriate height and is not at any angle relative to the horizontal.

When not in use, the height measuring bar 80, and incorporated date stamp housing 90 and date stamp 150 can be rotated so that they are parallel to the frame section 20 and 30 and therefore, do not protrude out of the frame where it can be accidentally hit by someone passing by.

Therefore, through use of the present invention, the device facilitates removable attachment to a vertical surface such as a wall 600 with a pair of oppositely disposed different measuring denominations 22 and 32 and a slidable frame assembly 70 retaining a height measuring device 80 with a housing 100 incorporating a date stamp 150 which cannot fall out of the housing so that the date stamp is permanently retained within the housing and can be inked so that the date that a given height is taken is marked into the planar surface 50 for permanent recordation of the child's height on a given date. The child can be measured on a monthly, bimonthly, quarterly, semi-annually or annual basis at the desire of the parent.

By taking sequential measurements, this can also be reported to the child's pediatrician so that the pediatrician can determine if the child is growing at a normal rate.

The present invention also facilitates easy relocation to a different location by the removable affixation members 14A through 14U and the folding member 60 by which the device can be folded in on itself for easy transport.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A wall-mounted height measuring device, comprising:
a. a first vertically aligned frame section and a spaced apart oppositely disposed vertically aligned second frame section which support a planar vertical section between them, to one side of the planar vertical section is a first vertical height measuring scale inscribed into the planar vertical section adjacent the first vertically aligned frame section, which first vertical height measuring scale extends from a bottom of the wall mounted measuring device to a top of the wall mounted measuring device and adjacent the second vertically aligned frame member is a second vertical height measuring scale inscribed into the planar vertical section and extending from the bottom to the top of the wall mounted measuring device;
b. in between the two vertical measuring scales on the vertical planar section is a clear planar surface onto which dates can be stamped to correspond to given heights on the vertical measuring scales, a foldable mechanism at an approximate midpoint of the height measuring device to facilitate transportation of the height measuring device from one wall location to another wall location;
c. the height measuring device including a rear surface having a multiplicity of spaced apart movable mounting means by which the height measuring device is removably affixed to a vertical surface;
d. a movable height level retaining frame member having a first outer sidewall section which is wrapped around and slidably press fit onto first vertically aligned frame section and a parallel oppositely disposed second outer sidewall section which is wrapped around and slidably press fit onto the second vertically aligned frame section so that the movable height level retaining frame member is slid up and down the first and second vertically aligned frame sections and remain affixed at a given section location on the height measuring device, the movable height level retaining frame member having a body comprising a first interior sidewall parallel to and adjacent the first outer sidewall section, a second interior sidewall parallel to and adjacent to the second outer sidewall section, a first upper transverse wall interconnecting the interior sidewalls and a parallel second lower transverse wall interconnecting the interior sidewalls, the first interior sidewall retains a first transverse retainer with an opening to receive a transverse round pin extending from a housing sidewall and the second interior sidewall retaining a second transverse retainer with an opening to receive a transverse round pin extending from a housing sidewall, the housing is rotatable about the round pins so that the housing can be retained perpendicular to the movable height level retaining frame member when in use or retained parallel to height level retaining frame member when not in use;
e. the movable height level retaining frame rotatably supporting a height measuring bar so that the height measuring bar can be rotated so that it is vertically oriented and parallel to the vertically aligned frame sections when not in use and can be rotated so that it is generally perpendicular to the vertically aligned frame sections when in use, incorporated into and made a part of the height measuring bar is a date stamp retaining housing having a stamp mechanism retaining chamber surrounded by sidewalls and a rear wall, a date stamp retaining assembly comprises a body with a thumb grip and with sidewalk surrounding an interior chamber which retains a date stamp having a date rotating mechanism to change the month, day and year, the sidewalls contain respective slots which slide on interior retaining pins, the date stamp extends to an open wall section between sidewalls so that when the sidewalls are pulled out of the date stamp retaining housing by a thumb pressure pulling on a grip, the date stamp retaining assembly is moved along slots so that the date stamp is aligned with the open wall and when the height measuring bar is rotated to a horizontal alignment perpendicular to the vertically aligned frame sections, the date stamp can come in contact with clear planar surface, the date stamp retaining housing retains the date stamp so that the date stamp cannot fall out and so that the date stamp can be inked when necessary to stamp a given date onto the clear planar surface; and
f. the height measuring device is removably affixed to a wall so that a child stands against the vertically aligned frame sections, the height measuring bar is rotated so that it is perpendicular to the vertically aligned frame sections and perpendicular to the interior sidewalls of the movable frame member, the first and second sections of the movable frame member are respectively slid on the vertically aligned frame sections so that the height measuring bar extends above a height of the child and then the movable frame member is slid down the vertically aligned frame sections so that the height measuring bar rests immediately above the child's head, the date stamp housing is pulled forward from the date stamp retaining housing so that the date stamp can affix the date onto the planar surface so that the child's given height on a certain day is recorded.

2. The wall-mounted height measuring device in accordance with claim 1, further comprising:
   a. when not in use, the height measuring bar and incorporated date stamp housing and date stamp can be rotated so that they are parallel to the vertically aligned frame sections and therefore, do not protrude out of the device.

3. The wall-mounted height measuring device in accordance with claim 1, further comprising: the first vertical height measuring scale is in inches.

4. The wall-mounted height measuring device in accordance with claim 1, further comprising: the second vertical height measuring scale is in centimeters.

5. The wall-mounted height measuring device in accordance with claim 1, further comprising;
   a. there is a given distance between a bottom of the height measuring bar and a height orientation of the date stamp; and
   b. the height measuring device is positioned by the same given distance above the horizontal surface on which the child stands to compensate for this difference between the bottom of the height measuring bar and the height of the date stamp.

6. The wall-mounted height measuring device in accordance with claim 1, further comprising;
   a. the moveable height leveling retaining frame is rotatable in a manner such that its interior edge abuts against the first interior sidewall and second interior sidewall of the moveable height leveling retaining frame so that the date stamp retaining housing is exactly press fit against the first interior sidewall and second interior sidewall of the moveable height level retaining frame so that the height measuring bar is exactly perpendicular to the moveable height level retaining frame; and
   b. the relative movement of the height level retaining frame being pressed against the moveable height level retaining member assures that the date stamp will be absolutely perpendicular to the planar surface to assure an accurate marking of the date.

7. A height measuring device comprising:
   a. a removable attachment to a vertical surface with a pair of oppositely disposed different measuring denominations and a slidable frame assembly retaining a height measuring bar incorporating a housing retaining a date stamp which cannot fall out of the housing so that the date stamp is permanently retained within the housing and is inked, the height measuring bar located on top of the head of a person standing against the device so that the date that a given height is taken is marked into a planar surface between the measuring denominations for a permanent recordation of a person's height on a given date.

8. A wall-mounted height measuring device, comprising:
   a. a first vertically aligned frame section and a spaced apart oppositely disposed vertically aligned second frame section which support a planar vertical section between them, to one side of the planar vertical section is a first vertical height measuring scale adjacent the first vertically aligned frame section, and adjacent the second vertically aligned frame member is a second vertical height measuring scale;
   b. in between the two vertical measuring scales on the vertical planar section is a clear planar surface onto which dates can be stamped to correspond to given heights on the vertical measuring scales;
   c. the height measuring device including a rear surface having mounting members by which the height measuring device is removably affixed to a vertical surface;
   d. a movable height level retaining frame member having a first outer sidewall section which is wrapped around and slidably press fit onto first vertically aligned frame section and a parallel oppositely disposed second outer sidewall section which is wrapped around and slidably press fit onto the second vertically aligned frame section so that the movable height level retaining frame member is slid up and down the first and second vertically aligned frame sections and remain affixed at a given section location on the height measuring device, the movable height level retaining frame member having a body rotatably supporting a height measuring bar so that the height measuring bar can be rotated so that it is vertically oriented and parallel to the vertically aligned frame sections when not in use and can be rotated so that it is generally perpendicular to the vertically aligned frame sections when in use, incorporated into and made a part of the height measuring bar is a date stamp retaining housing retaining a date stamp retained within the date stamp retaining housing when not in use and movable to a position against the clear planar surface when in use, the date stamp retained within the date stamp retaining housing so that the date stamp cannot fall out of the date stamp retaining housing; and
   e. the height measuring device is removably affixed to a wall so that a child stands against the vertically aligned frame sections, the height measuring bar is rotated so that it is perpendicular to the vertically aligned frame sections and perpendicular to the movable frame member, the first and second sections of the movable frame member are respectively slid on the vertically aligned frame sections so that the height measuring bar extends above a height of the child and then the movable frame member is slid down the vertically aligned frame sections so that the height measuring bar rests immediately above the child's head, the date stamp is moved against the clear planar surface so that the date stamp is used to affix the date onto the clear planar surface so that the child's given height on a certain day is recorded.

9. The wall-mounted height measuring device in accordance with claim 8, further comprising:
   a. when not in use, the height measuring bar and incorporated date stamp housing and date stamp can be rotated so that they are parallel to the vertically aligned frame sections and therefore, do not protrude out of the device.

10. The wall-mounted height measuring device in accordance with claim 8, further comprising: the first vertical height measuring scale is in inches.

11. The wall-mounted height measuring device in accordance with claim 8, further comprising: the second vertical height measuring scale is in centimeters.

12. The wall mounted height measuring device in accordance with claim 8, further comprising: a foldable mechanism at an approximate midpoint of the height measuring device to enable the height measuring device to be folded in half for easy transport.

13. The wall-mounted height measuring device in accordance with claim 8, further comprising;
   a. there is a given distance between a bottom of the height measuring bar and a height orientation of the date stamp; and
   b. the height measuring device is positioned by the same given distance above the horizontal surface on which the child stands to compensate for this difference between the bottom of the height measuring bar and the height of the date stamp.

14. The wall-mounted height measuring device in accordance with claim 8, further comprising;
   a. the moveable height leveling retaining frame is rotatable in a manner such that its interior edge abuts against the first interior sidewall and second interior sidewall of the moveable height leveling retaining frame so that the date stamp retaining housing is exactly press fit against the first interior sidewall and second interior sidewall of the moveable height level retaining frame so that the height measuring bar is exactly perpendicular to the moveable height level retaining frame; and
   b. the relative movement of the height level retaining frame being pressed against the moveable height level retaining member assures that the date stamp will be absolutely perpendicular to the planar surface to assure an accurate marking of the date.

15. A height measuring device, comprising:
   a. a portable foldable height measuring device which is removably mounted to a vertical surface in order to measure the height growth of a person who stands against the device;
   b. the height measuring device includes a pair of oppositely disposed vertical frame members with a parallel set of oppositely disposed height measurement scales, the height measuring scales separated by a vertical marking surface so that a given date can be stamped at the location of a given height in order to record the growth of a person; and
   c. press fit vertical sliding bars movably attached to the respective vertical frames in a press fit manner so that the sliding bars can be slid up or down the distance of the vertical frames and remain stationary at a given point, the pair of sliding bars rotatably supporting a height measuring bar which has a planar surface and contains thereon a housing to permanently retain a stamping mechanism to record dates, the housing contains a mechanism by which the stamp is permanently retained within the housing so that the same stamp can be used over and over again to record the changes in a person's height without the concern that the stamp will be lost or mislaid or modified to give an inaccurate reading.

* * * * *